| United States Patent [19] | [11] Patent Number: 4,590,282 |
| Henrick | [45] Date of Patent: May 20, 1986 |

[54] PEST CONTROL AGENTS

[75] Inventor: Clive A. Henrick, Palo Alto, Calif.

[73] Assignee: Sandoz Ltd., Basel, Switzerland

[21] Appl. No.: 653,277

[22] Filed: Sep. 24, 1984

[51] Int. Cl.$^4$ ............................................ C07D 317/00
[52] U.S. Cl. ...................................... 549/453; 549/451
[58] Field of Search ...................... 549/451, 453, 454

[56] References Cited

U.S. PATENT DOCUMENTS 3,936,470  2/1976  Heeres ................................. 549/455
4,423,071  12/1983  Chignac et al. ..................... 549/454

Primary Examiner—Ethel G. Love
Attorney, Agent, or Firm—Jacqueline S. Larson; Hana Dolezalova

[57] ABSTRACT

Dioxolane and benzodioxin derivatives, intermediates therefor, synthesis thereof, and the use of the compounds for the control of pests.

13 Claims, No Drawings

PEST CONTROL AGENTS

The present invention relates to novel dioxolane and benzodioxin derivatives, intermediates therefor, synthesis thereof, and the use of the compounds for the control of pests.

More particularly, the compounds of the present invention are represented by the following formulas (A) and (B):

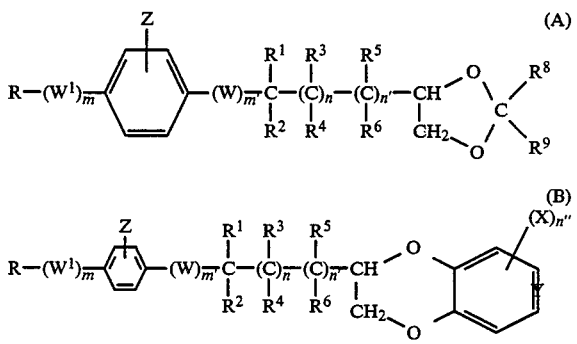

wherein,
each of m and m' is independently zero or one;
each of n and n' is zero, one or two;
n" is zero, one, two, three or four;
R is hydrogen, lower alkyl, lower alkenyl, lower alkynyl, lower haloalkyl, lower haloalkenyl, lower haloalkynyl, lower alkoxyalkyl, lower alkylthioalkyl, cycloalkyl, halocycloalkyl, cycloalkylalkyl, heterocycloalkyl, or heterocycloalkylalkyl;
each of $R^1$, $R^2$, $R^3$, $R^4$, $R^5$, $R^6$ and $R^7$ is independently hydrogen or lower alkyl, provided that: (1) when n is one and n' is zero, then $R^2$ and $R^4$ can together form a polymethylene bridge of two to four carbon atoms, or (2) when each of n and n' is one, then either $R^2$ and $R^4$ or $R^4$ and $R^6$ or $R^2$ and $R^6$ can together form a polymethylene bridge of two to four carbon atoms;
$R^8$ is hydrogen or lower alkyl;
$R^9$ is hydrogen, lower alkyl, cycloalkyl, or the radical

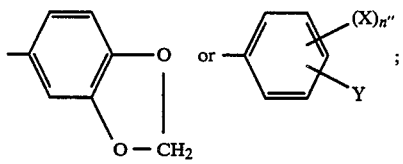

W is oxygen, sulfur, $NR^7$ or carbonyl;
$W^1$ is oxygen, sulfur, sulfinyl, sulfonyl, $NR^7$ or carbonyl;
each of X and Y is independently hydrogen, lower alkyl, lower alkenyl, lower alkynyl, lower alkoxy, lower alkoxyalkyl, lower alkylthio, lower alkylthioalkyl, lower haloalkyl, lower haloalkenyl, lower haloalkynyl, cycloalkyl or halogen; and
Z is hydrogen, lower alkyl, lower haloalkyl or halogen.

In the description hereinafter and the appended claims, each of m, m', n, n', n", R—$R^9$, W, $W^1$, X, Y and Z is as defined above, unless otherwise specified.

The compounds of the present invention of formula A can be prepared by methods known in the art, such as those described in U.S. Pat. No. 4,100,296, for example, as outlined below:

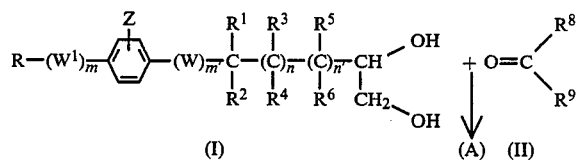

In the above synthesis, a diol of formula I is reacted with a carbonyl compound of formula II in the presence of an acid catalyst and at a temperature of generally between 40° and 150° C., in an inert solvent such as benzene, toluene, ether or chloroform. All acid compounds or Lewis acids which are customarily used for acetylation reactions, for example, p-toluenesulfonic acid or phosphoric acid, can be used as catalysts.

Alternatively, a diol of formula I is reacted with an acetal or ketal compound (III; $R^{10}$ is methyl or ethyl) in the presence of an acid catalyst and at a temperature generally of 40° to 150° C.

Compounds of the present invention of formula B can be prepared by the reaction of a phenol, thiophenol or aniline (IV) with sodium hydride and then with a halide or methanesulfonate (V; Q is a halo atom or mesyloxy group), in an organic solvent such as N-methylpyrrolidone, dimethylformamide or tetrahydrofuran and at room temperature or below.

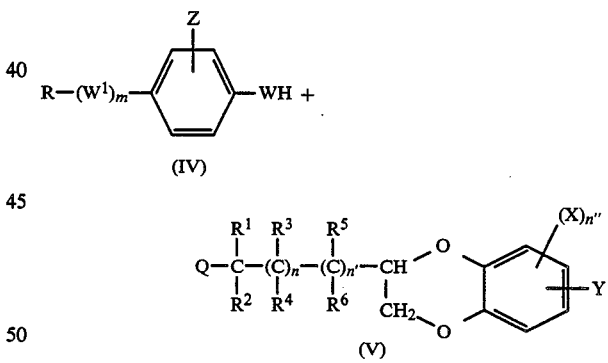

Compounds of formulas A and B where $W^1$ is sulfinyl are prepared by reacting a compound of formula A or B where $W^1$ is sulfur with one equivalent of sodium periodate or m-chloroperbenzoic acid in a solvent such as methanol or methylene chloride. Compounds where $W^1$ is sulfonyl are prepared in the same manner, except that two equivalents of m-chloroperbenzoic acid are used. Alternatively, either hydrogen peroxide in warm acetic acid or excess hydrogen peroxide and selenium dioxide is used as the oxidant.

The starting materials of formulas I through V are known compounds, or they can be produced by methods analogous to known methods described in the literature. Thus, for example, a compound of formula I can be obtained as follows:

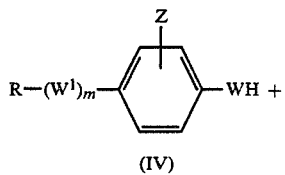

(IV)

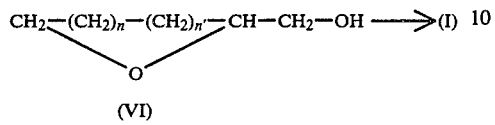

(VI)

The compounds of the present invention of formulas A and B can have one or more asymmetric carbon atoms. The present invention includes each of the optical isomers and isomeric mixtures thereof. In the examples hereinafter, where applicable and unless otherwise specified, the compound is a mixture of stereo isomers.

The compounds of the present invention of formulas A and B are useful pest control agents, particularly for the control of insects, mites and ticks. The utility of these compounds as pest control agents is believed to be attributable to their juvenile hormone activity. They are preferably applied to the immature pest, namely during the embryo, larval or pre-pupal stage, in view of their effect on metamorphosis and otherwise abnormal development leading to death or inability to reproduce. These compounds can be effective control agents for insects of, for example, the orders Lepidoptera, Hemiptera, Homoptera, Coleoptera, Diptera, Orthoptera, and Siphonaptera, and other insects, and mites and ticks of the class Acari, including mites of the families Tetranychidae and Tarsonomidae and ticks of the family Argasidae and Ixodidae. The compounds can be applied to the pest or its locus in a pest controlling amount, usually of the order of 0.1 μg to 100 μg per insect, mite or tick.

In the use of the compounds of formulas A and B for combatting pests, a compound of formula A or B, or mixtures thereof, can be combined with a carrier substance for application to the pest or its locus. The carrier can be liquid or solid and include adjuvants such as wetting agents, dispersing agents and other surface active agents. The compounds can be used in formulations such as wettable powders, solutions, dusts, granules, emulsifiable concentrates and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to 90.0 percent, by weight. Generally, a concentration of less than 25 percent of the active compound is employed.

The compounds of formula A or B can be combined with a cyclodextrin to make a cyclodextrin inclusion complex for application to the pest or its locus.

The compounds of the present invention can be used in combination with other pesticides such as the synthetic pyrethroids, carbamates, phosphates and insect growth regulators, or with insect attractants.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to six halogen atoms.

The term "lower alkenyl" refers to an alkenyl group, straight or branched, having a chain length of two to eight carbon atoms and one or two ethylenic bonds. The term "lower haloalkenyl" refers to a lower alkenyl group substituted with one to six halogen atoms.

The term "lower alkynyl" refers to an alkynyl group, straight or branched, having a chain length of two to eight carbon atoms and one or two acetylenic bonds. The term "lower haloalkynyl" refers to a lower alkynyl group substituted with one to six halogen atoms.

The term "lower alkoxy" refers to an alkoxy group, straight or branched, having a chain length of one to eight carbon atoms.

The term "lower alkoxyalkyl" refers to an alkyl group substituted at one of the carbon atoms by an alkoxy group, straight or branched, the total number of carbon atoms being not greater than ten.

The term "lower alkylthio" refers to an alkylthio group, straight or branched, having a chain length of one to eight carbon atoms.

The term "lower alkylthioalkyl" refers to a lower alkyl group substituted at one of the carbon atoms by an alkylthio group, straight or branched, the total number of carbon atoms being not greater than ten.

The term "cycloalkyl" refers to a cycloalkyl group of three to eight cyclic carbon atoms. The term "cycloalkylalkyl" refers to a cycloalkyl group wherein one hydrogen atom is replaced by a lower alkyl group, the total number of carbon atoms being from four to twelve. The term "halocycloalkyl" refers to a cycloalkyl group substituted with one to three halogen atoms.

The term "heterocycloalkyl" refers to a heterocycloalkyl group, saturated or unsaturated, of two to six carbon atoms and one to three atoms selected from nitrogen, oxygen or sulfur. The term "heterocycloalkylalkyl" refers to a heterocycloalkyl group wherein one hydrogen is replaced by a lower alkyl group, the total number of carbon atoms being from three to twelve.

The following examples are provided to illustrate the practice of the present invention. Temperature is given in degrees Centigrade. "RT" stands for room temperature.

EXAMPLE 1

A mixture of 3-[4-(1-methylpropoxy)phenoxy]-1,2-propanediol (1.0 g, 4.2 mmol), acetone (0.24 g, 4.2 mmol) and p-toluenesulfonic acid (0.03 g) in 20 ml of petroleum ether is heated under reflux for 7 hours. Water generated from the reaction is removed. The final solution is concentrated to remove the solvent and the product is purified by column chromatography to give 2,2-dimethyl-4-[4-(1-methylpropoxy)phenoxymethyl]-1,3-dioxolane, MS m/e 280 (M+).

nmr (CDCl$_3$): δ 6.85 (s, 4H, aromatic H's), 3.70–4.65 (m, 6H, CH$_3$—CH$_2$—C$\underline{H}$(CH$_3$)—O—,

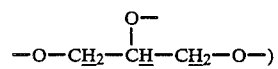

and 0.80–2.00 ppm (m, 14H, CH₃—CH₂—CH(CH₃)—O—, >C(CH₃)₂).

EXAMPLE 2

A mixture of 3-[4-(1-methylpropoxy)phenoxy-1,2-propanediol (1.50 g, 6.3 mmol), 4-chlorobenzaldehyde (0.8 g, 5.7 mmol) and a catalytic amount of p-toluenesulfonic acid (monohydrate, 0.02 g, 0.1 mmol) in 20 ml of petroleum ether is heated under reflux for 6.5 hours. Water generated from the reaction is removed. The solvent is removed under vacuum and the product is purified by column chromatography to give two separate isomeric mixtures of 2-(4-chlorphenyl)-4-[4-(1-methylpropoxy)phenoxymethyl]-1,3-dioxolane, MS m/e 362 (M+).

nmr (CDCl₃): δ 7.35 (s, 4H, aromatic H's), 6.80 (s, 4H, aromatic H's), 5.90 (s, 1H, —O—CH—O—), 3.50–4.70 (m, 6H, CH₃—CH₂—CH(CH₃)—O—,

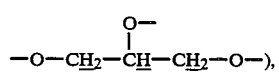

0.80–2.00 ppm (m, 8H, CH₃—CH₂—CH(CH₃)—O—).

EXAMPLE 3

Following the procedure of Example 2, 3-[4-(1-methylpropoxy)phenoxy]-1,2-propanediol is reacted with each of the carbonyl compounds under column I to yield the corresponding dioxolane under column II.

I.

1. 2,4-dichlorobenzaldehyde
2. 4-methylbenzaldehyde
3. 4-isopropylbenzaldehyde
4. 4-methoxybenzaldehyde
5. acetophenone
6. 4-methylacetophenone
7. 2-butanone
8. cyclohexyl methyl ketone
9. propyl n-butyl ketone
10. 3,4-methylenedioxybenzaldehyde
11. propionophenone

II.

1. 2-(2,4-dichlorophenyl)-4-[4-(1-methylpropoxy)phenoxymethyl]-1,3-dioxolane
2. 2-(4-methylphenyl)-4-[4-(1-methylpropoxy)phenoxymethyl]-1,3-dioxolane
3. 2-(4-isopropylphenyl)-4-[4-(1-methylpropoxy)phenoxymethyl]-1,3-dioxolane
4. 2-(4-methyoxyphenyl)-4-[4-(1-methylpropoxy)phenoxymethyl]-1,3-dioxolane
5. 2-methyl-2-phenyl-4-[4-(1-methylpropoxy)phenoxymethyl]-1,3-dioxoland
6. 2-methyl-2-(4-methylphenyl)-4-[4-(1-methylpropoxy)phenoxymethyl]-1,3-dioxolane
7. 2-ethyl-2-methyl-4-[4-(1-methylpropoxy)phenoxymethyl]-1,3-dioxolane
8. 2-cyclohexyl-2-methyl-4-[4-(1-methylpropoxy)phenoxymethyl]-1,3-dioxolane
9. 2-n-butyl-2-phenyl-4-[4-(1-methylpropoxy)phenoxymethyl]-1,3-dioxolane
10. 2-(3,4-methylenedioxyphenyl)-4-(1-methylpropoxy)phenoxymethyl]-1,3-dioxolane
11. 2-ethyl-2-phenyl-4-[4-(1-methylpropoxy)phenoxymethyl]-1,3-dioxolane.

EXAMPLE 4

Following the procedure of Example 2, 4-chlorobenzaldehyde is reacted with each of the diols under column III to give the corresponding dioxolane under column IV.

III.

12. 3-[4-(3-methyl-2-butenoxy)phenoxy]-1,2-propanediol
13. 3-[4-(1-methylbutoxy)phenoxy]-1,2-propanediol
14. 3-[4-(3-methoxy-3-methylbutoxy)phenoxy]-1,2-propanediol
15. 3-[4-(3-chloro-2-propenoxy)phenoxy]-1,2-propanediol
16. 3-(4-cyclobutoxyphenoxy)-1,2-propanediol
17. 3-[4-(1-methylpropylthio)phenoxy]-1,2-propanediol
18. 3-[4-(1-methylpropylthio)phenylthio]-1,2-propanediol
19. 3-[2-fluoro-4-(1-methylpropoxy)phenoxy]-1,2-propanediol
20. 3-[3-chloro-4-(1-methylpropoxy)phenoxy]-1,2-propanediol
21. 3-[3-methyl-4-(1-methylpropoxy)phenoxy]-1,2-propanediol
22. 3-[4-(1-methylpropoxy)-5-trifluoromethylphenoxy]-1,2-propanediol
23. 4-[4-(1-methylpropoxy)phenoxy]-1,2-butanediol
24. 4-[4-(1-methylpropoxy)phenoxy]-1,2-pentanediol
25. 3-[4-(1-methylpropoxy)phenoxy]-1,2-butanediol
26. 5-[4-(1-methylpropoxy)phenoxy]-1,2-pentanediol.

IV.

12. 2-(4-chlorophenyl)-4-[4-(3-methyl-2-butenoxy)phenoxymethyl]-1,3-dioxolane
13. 2-(4-chlorophenyl)-4-[4-(1-methylbutoxy)phenoxymethyl]-1,3dioxolane
14. 2-(4-chlorophenyl)-4-[4-(3-methoxy-3-methylbutoxy)phenoxymethyl]-1,3-dioxolane
15. 2-(4-chlorophenyl)-4-[4-(3-chloro-2-propenoxy)phenoxymethyl]-1,3-dioxolane
16. 2-(4-chlorophenyl)-4-[(4-cyclobutoxyphenoxy)methyl]-1,3-dioxolane
17. 2-(4-chlorophenyl)-4-[4-(1-methylpropylthio)phenoxymethyl]-1,3-dioxolane
18. 2-(4-chlorophenyl)-4-[4-(1-methylpropylthio)phenylthiomethyl]-1,3-dioxolane
19. 2-(4-chlorophenyl)-4-[2-fluoro-4-(1-methylpropoxy)phenoxymethyl]-1,3-dioxolane
20. 2-(4-chlorophenyl)-4-[3-chloro-4-(1-methylpropoxy)phenoxymethyl]-1,3-dioxolane
21. 2-(4-chlorophenyl)-4-[3-methyl-4-(1-methylpropoxy)phenoxymethyl]-1,3-dioxolane
22. 2-(4-chlorophenyl)-4-[4-(1-methylpropoxy)-5-trifluoromethylphenoxymethyl]-1,3-dioxolane
23. 2-(4-chlorophenyl)-4-{2-[4-(1-methylpropoxy)phenoxy]ethyl}-1,3-dioxolane
24. 2-(4-chlorophenyl)-4-{2-[4-(1-methylpropoxy)phenoxy]propyl}-1,3-dioxolane
25. 2-(4-chlorophenyl)-4-{1-[4-(1-methylpropoxy)phenoxy]ethyl }-1,3-dioxolane
26. 2-(4-chlorophenyl)-4-{3-[4-(1-methylpropoxy)phenoxy]propyl}-1,3-dioxolane

EXAMPLE 5

To a solution of 2-(4-chlorophenyl)-4-[4-(1-methylpropylthio)phenoxymethyl]-1,3-dioxolane (7.1 mmol) in 10 ml of methanol at 0° is added, dropwise over 5 min., sodium m-periodate (1.67 g, 7.8 mmol) in 13 ml of water. The mixture is stirred for 3 hours while warming to RT. The reaction mixture is poured into water and extracted with ether. The combined organic extracts are washed with saturated sodium thiosulfate, with water and with brine, dried and rotoevaporated to give 2-(4-chlorophenyl)-4-[4-(1-methylpropylsulfinyl)-phenoxymethyl]-1,3-dioxolane.

7.1 Mmol of 2-(4-chlorophenyl)-4-[4-(1-methyl-propylthio)phenoxymethyl]-1,3-dioxolane is reacted with 15.6 mmol of m-chloroperbenzoic acid in chloroform to yield 2-(4-chlorophenyl)-4-[4-(1-methylpropyl-sulfonyl)phenoxymethyl]-1,3-dioxolane. Alternatively, either hydrogen peroxide in warm acetic acid or excess hydrogen peroxide and selenium dioxide in methanol is used as the oxidant.

EXAMPLE 6

Following the procedure of Example 1 or 20, 3-[4-(1-methylpropoxy)phenoxy]-1,2-butanediol is reacted with each of acetone and benzaldehyde to yield, respectively, 2,2-dimethyl-4-{1-[4-(1-methylpropoxy)phenoxy]e-thyl}-1,3-dioxolane, and 2-phenyl-4-{1-[4-(1-methylpropoxy)phenoxy]ethyl}-1,3-dioxolane.

In the same manner, 3-[4-(1-methylpropoxy)phenox-y]-1,2-pentanediol is reacted with each of acetone and benzaldehyde to give, respectively, 2,2-dimethyl-4-{1-[4-(1-methylpropoxy)phenoxy]-propyl}-1,3-dioxolane, and 2-phenyl-4-{1-[4-(1-methylpropoxy)phenoxy]propyl}-1,3-dioxolane.

EXAMPLE 7

To sodium hydride (0.53 g, 50% in oil, 11.0 mmol) in 40 ml of DMF, under $N_2$ at 5°, is added, dropwise and with vigorous stirring, a solution of 4-(1-methylpropoxy)phenol (1.66 g, 10.0 mmol) in 10 ml of DMF. After the mixture is stirred at RT for 1 hour, a solution of 2-mesyloxymethyl-1,4-benzodioxin (2.70 g, 11.0 mmol) in 10 ml of DMF is slowly added. The resulting reaction mixture is stirred at RT for 48 hours and is then mixed with water and extracted with ether. The combined organic extracts are washed with water and with brine, dried and solvent removed and the product is purified by column chromatography to give 2-[4-(1-methyl-propoxy)phenoxymethyl]-1,4-benzodioxin, MS m/e 315 (M+).

nmr (CDCl$_3$): δ 0.8–2.0 (m, 8H, CH$_3$—C$\underline{H}_2$—CH(CH$_3$)—O), 3.9–4.7 (m, H, C$\underline{H}$(CH$_3$)—$\overline{O}$,

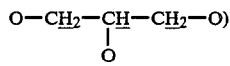

and 6.8 ppm (ss, 8H, aromatic).

EXAMPLE 8

Following the procedure of Example 7, each of the phenols or thiophenols under column V is reacted with 2-mesyloxymethyl-1,4-benzodioxin to give the corresponding 2-substituted benzodioxin under column VI.

V.

27. 4-(3-methyl-2-butenoxy)phenol
28. 4-(1-methylbutoxy)phenol
29. 4-(3-methoxy-3-methylbutoxy)phenol
30. 4-(3-chloro-2-propenoxy)phenol
31. 4-cyclobutoxyphenol
32. 4-(1-methylpropylthio)phenol
33. 4-(1-methylpropylthio)thiophenol.

VI.

27. 2-[4-(3-methyl-2-butenoxy)phenoxymethyl]-1,4-benzodioxin
28. 2-[4-(1-methylbutoxy)phenoxymethyl]-1,4-benzodioxin
29. 2-[4-(3-methoxy-3-methylbutoxy)phenoxymethyl]-1,4-benzodioxin
30. 2-[4-(3-chloro-2-propenoxy)phenoxymethyl]-1,4-benzodioxin
31. 2-(4-cyclobutoxyphenoxymethyl)-1,4-benzodioxin
32. 2-[4-(1-methylpropylthio)phenoxymethyl]-1,4-benzodioxin
33. 2-[4-(1-methylpropylthio)phenylthiomethyl]-1,4-benzodioxin.

EXAMPLE 9

Following the procedure of Example 7, 4-(1-methyl-propoxy)phenol is reacted with each of the benzodioxins under column VII to yield the corresponding 2-substituted benzodioxin under column VIII.

VII.

34. 2-(2-mesyloxyethyl)-1,4-benzodioxin
35. 2-(2-mesyloxypropyl)-1,4-benzodioxin
36. 2-(1-mesyloxyethyl)-1,4-benzodioxin
37. 2-(1-mesyloxypropyl)-1,4-benzodioxin
38. 2-(3-mesyloxypropyl)-1,4-benzodioxin

VIII.

34. 2-{2-[4-(1-methylpropoxy)phenoxy]ethyl}-1,4-benzodioxin
35. 2-{2-[4-(1-methylpropoxy)phenoxy]propyl}-1,4-benzodioxin
36. 2-{1-[4-(1-methylpropoxy)phenoxy]ethyl}-1,4-benzodioxin
37. 2-{1-[4-(1-methylpropoxy)phenoxy]propyl}-1,4-benzodioxin
38. 2-{3-[4-(1-methylpropoxy)phenoxy]propyl}-1,4benzodioxin.

What is claimed is:

1. A compound of the formula (A):

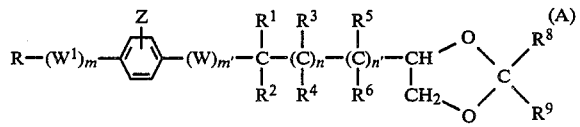

wherein,
each of m and m' is one;
each of n and n' is independently zero, one or two;
n" is zero, one two, three or four;
R is lower alkyl, lower alkenyl, lower alkynyl, lower haloalkyl, lower haloalkenyl, lower haloalkynyl, lower alkoxyalkyl, lower alkylthioalkyl, cycloalkyl, halocycloalkyl, or cycloalkylalkyl;
each of $R^1$, $R^2$, $R^3$, $R^4$, $R^5$, $R^6$ and $R^7$ is indpendently hydrogen or lower alkyl;
$R^8$ is hydrogen or lower alkyl, provided that: when $R^9$ is other than hydrogen or lower alkyl, then $R^8$ cannot be lower alkyl;

R⁹ is hydrogen, lower alkyl, cycloalkyl or the radical

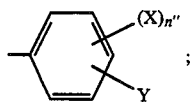

W is oxygen, sulfur, NR⁷ or carbonyl;
W¹ is oxygen, sulfur, sulfinyl, sulfonyl, NR⁷ or carbonyl;
each of X and Y is independently hydrogen, lower alkyl, lower alkenyl, lower alkynyl, lower alkoxy, lower alkoxyalkyl, lower alkylthio, lower alkylthioalkyl, lower haloalkyl, lower haloalkenyl, lower haloalkynyl, cycloalkyl or halogen; and
Z is hydrogen, lower alkyl, lower haloalkyl or halogen.

2. A compound of the following formula, according to claim 1:

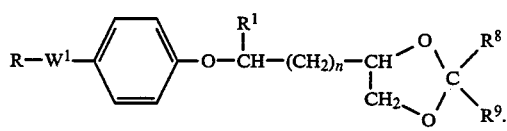

3. A compound according to claim 2 wherein n is zero or one, R¹ is hydrogen or methyl and W¹ is oxygen or sulfur.

4. A compound according to claim 3 wherein R is lower alkyl, lower alkenyl or lower alkoxyalkyl.

5. A compound according to claim 4 wherein n is zero and R¹ is hydrogen.

6. A compound according to claim 5 wherein R⁸ is hydrogen or methyl and R⁹ is lower alkyl.

7. A compound according to claim 6 wherein R is 1-methylpropyl or 3-methyl-2-butenyl.

8. The compound 2,2-dimethyl-4-[4-(1-methylpropoxy)phenoxymethyl]-1,3-dioxolane, according to claim 7.

9. A compound according to claim 5 wherein R⁸ is hydrogen, and R⁹ is the radical

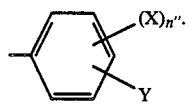

10. A compound according to claim 9 wherein R is 1-methylpropyl or 3-methyl-2-butenyl.

11. A compound according to claim 10 wherein n'' is one, X is halogen and is in the ortho position and Y is methyl, ethyl, isopropyl, methoxy or halogen and is in the para position.

12. A compound according to claim 10 wherein n'' is zero and Y is methyl, ethyl, isopropyl, methoxy or halogen and is in the para position.

13. The compound 2-(4-chlorophenyl)-4-[4-(1-methyl-propoxy)phenoxymethyl]-1,3-dioxolane, according to claim 12.